United States Patent [19]
Imamura et al.

[11] Patent Number: 6,143,560
[45] Date of Patent: Nov. 7, 2000

[54] METHOD OF SYNCHRONIZING EPITHELIAL CELLS INTO $G_0$ PHASE

[75] Inventors: Mio Imamura; Yasuharu Itagaki; Morimasa Tanimoto, all of Sapporo, Japan

[73] Assignee: Snow Brand Milk Products Co., Ltd., Hokkaido, Japan

[21] Appl. No.: 09/179,525

[22] Filed: Oct. 27, 1998

[30] Foreign Application Priority Data

Oct. 28, 1997 [JP] Japan ........................... 9-296014

[51] Int. Cl.[7] ........................... C12N 5/00
[52] U.S. Cl. ................ 435/376; 435/377; 435/375; 435/383
[58] Field of Search .................. 435/376, 377, 435/375, 383

[56] References Cited

PUBLICATIONS

Jouvenot et al. Uterine epithelial cells in primary culture: a model system to study cell proliferation. Cell. Mol. Biol. 36(4): 421–427, 1990.

Sia et al. Quiescent mammary epithelial cells have reduced connexin43 but maintain a high level of gap junction intercellular communication. Dev. Genet. 24(1–2): 111–122, 1999.

Larsson et al. Immediate effects of serum depletion on dissociation between growth in size and cell division in proliferating 3T3 cells. J. Cell. Physiol. 127(2): 267–73, May, 1986.

Lehmann et al. Response of different mammary epithelial cell lines to a mammary derived growth factor. Biomed. Biochim. Acta 48 (1): 143–151, 1989.

Liu et al. Estimation of PCNA mRNA stability in cell cycle by a serum–deprivation method. Journal of Cellular Biochemistry 57: 641–646, 1995.

Zavizion et al. Effect of mammary–derived growth inhibitor on proliferation of MAC–T bovine mammary epithelial cells. J. Dairy Science 76(12): 3721–3726, Dec. 1993.

Zetterberg et al. Kinetic analysis of regulatory events in $G_1$ leading to proliferation or quiescence of Swiss 3T3 cells. Proc. Natl. Acas. Sci. USA 82: 5365–5369, Aug. 1985.

*Primary Examiner*—Leon B. Lankford, Jr.
*Attorney, Agent, or Firm*—Testa, Hurwitz & Thibeault, LLP

[57] ABSTRACT

The present invention relates to a method of synchronizing epithelial cells into $G_0$ phase, more specifically, a method of synchronizing epithelial cells into $G_0$ phase characterized by culturing the cells in a synthetic medium for 5 days or more, wherein said synthetic medium is a medium with the lowered concentration of bovine fetal serum 5% or less and said epithelial cells is bovine mammary gland cells. Further, the present invention relates to a method of culturing cells characterized by using $G_0$ phase synchronized cells obtained by the present invention, and a method of screening a related to differentiation and/or maturation of said cells by using $G_0$ phase synchronized cells. The present invention is useful for easily synchronizing epithelial cells into $G_0$ phase and for screening a factor related to differentiation and/or maturation of epithelial cells.

10 Claims, 1 Drawing Sheet

METHOD OF SYNCHRONIZING EPITHELIAL CELLS INTO $G_0$ PHASE

FIELD OF THE INVENTION

The present invention relates to a method of synchronizing epithelial cells into $G_0$ phase, characterized by culturing epithelial cells to confluence and keeping them cultured in a synthetic medium for 5 days or more, wherein said synthetic medium is a medium with the lowered concentration of bovine fetal serum 5% or less and said epithelial cells are bovine mammary epithelial cells. Further, the present invention relates to a method of culturing cells characterized by culturing $G_0$ phase synchronized cells obtained by the present invention and a method of screening a factor related to differentiation and maturation of the cells using said $G_0$ phase synchronized cells.

BACKGROUND OF THE INVENTION

Research on animal, that is cloned animal, with separated embryo has been carried out these days. Recently, a sheep "Dolly" of the Roslin Institute in England is known as an example of cloned animal derived from somatic cell. In this example, it was confirmed that $G_0$ phase synchronization of the cultured cells was very effective for synchronizing mitosis of cytoplasm of the recipient (embryo) and minimizing gene damage.

Further, research to find out a factor related to differentiation and maturation of various kinds of cell or inhibitory factor thereof has been carried out. For the above, it is necessary to control cell cycle of the cells into $G_0$ phase. $G_0$ phase synchronized cells have advantage of (1) responding clearly to growth factor and/or proliferation factor when the the cells are used as a model for the mechanism of cell in a living body, (2) minimizing gene damage when the cells are used as an donor of gene and (3) making their synchronization easy under the environments around the implanted cells.

Conventionally, there are serum restriction method or contact inhibition method as a method of synchronizing cells into $G_0$ phase. In serum restriction method, human normal diploid cells are cultured to confluence in a growth medium (ES medium, 10% bovine fetal serum), followed by changing the medium to serum restricted medium (ES medium, 0.5% bovine fetal serum) and keeping the cells cultured by replacing the medium into fresh one on day 2 and 4, and then replacing it into growth medium (10% serum) on day 6 so as to stimulate proliferation thereof Usually, it takes about 20 hours to return to the progress of cell cycle by the stimulation of proliferation thereof. However, time to return to the progress of cell cycle by serum concentration, serum restricted time and stimulation with serum is different with respect to characters of cell and, therefore, it is necessary to adjust the conditions to each cell type. On the other hand, in contact inhibition method, when normal adhesive cells are cultured in a dish or a flask for cell culture, cells grow until colonies contact each other or colonies contact the wall of the dish or the flask (confluent state) and mitosis stops. Many cells at that time are considered to be in $G_0$ phase of cell cycle. For example, cancer cell is considered to lose capability of contact inhibition and known to keep growing until colonies pile each other. However, in the case of bovine mammary gland epithelial cell, because $G_0$ phase synchronization was incomplete using only contact inhibition method, the other method to solve the above problem is expected to develop.

SUMMARY OF THE INVENTION

Considering these situations, the present inventors have studied eagerly and found a method of easily synchronizing bovine mammary gland epithelial cells by culturing them for 5 days or more in a synthetic medium with the lowered concentration of bovine fetal serum 5% or less. In addition, we also found it possible to screen a factor related to differentiation and/or maturation of said cell by using $G_0$ phase synchronized cell obtained by the present method. Accordingly, the object of the present invention is to provide a method of synchronizing epithelial cells into $G_0$ phase characterized by culturing epithelial cells into a dense state and keeping them cultured in a synthetic medium for 5 days or more, wherein said synthetic medium is a medium with the lowered concentration of bovine fetal serum 5% or less and said epithelial cell is bovine mammary gland cell. Further, another object of the present invention is to provide a method of culturing cells characterized by culturing $G_0$ phase synchronized cell obtained by the present invention and a method of screening a factor related to differentiation and/or maturation of said cell using $G_0$ phase synchronized cell.

Another object of the present invention is to provide a method of synchronizing epithelial cells into $G_0$ phase characterized by culturing epithelial cells into a dense state and keeping them cultured in a synthetic medium for 5 days or more, wherein said synthetic medium is a medium with the lowered concentration of bovine fetal serum 5% or less and said epithelial cell is bovine mammary gland epithelial cell.

Another object of the present invention is to provide a method of culturing cells characterized by culturing $G_0$ phase synchronized cell obtained by the present invention. Further, another object of the present invention is to provide a method of screening a factor related to differentiation and/or maturation of said cell.

The present invention is useful for easily synchronizing epithelial cell into $G_0$ phase and screening a factor related to differentiation and/or maturation of said epithelial cell.

DETAILED DESCRIPTION OF THE INVENTION AND PREFERRED EMBODIMENTS

Though cells used in the present invention are epithelial cells without any limitation, bovine mammary gland epithelial cells are especially preferable for the invention. According to a usual method, these epithelial cells are cultured into a dense state. Then, they are cultured for 5 days or more, preferably 6 days, in a synthetic medium. Said synthetic medium is preferably DMEM medium or MEM medium. And this medium comprises 5% or less, preferably 1%, of bovine fetal serum. Epithelial cells cultured like the above are synchronized into $G_0$ phase and clone can be easily prepared from somatic cells. Cells prepared like this can remedy the original cell state, that is, can become cells with normal cell cycle in an hour by stimulation with serum.

Further, a factor related to cell differentiation and/or maturation can be screened by using $G_0$ phase synchronized cell obtained by the present method.

The present invention will be described more specifically by showing examples which are merely exemplification and the scope of the present invention will not be limited by those examples.

Example 1
Preparation of $G_0$ Phase Synchronized Cells

Figure 1:
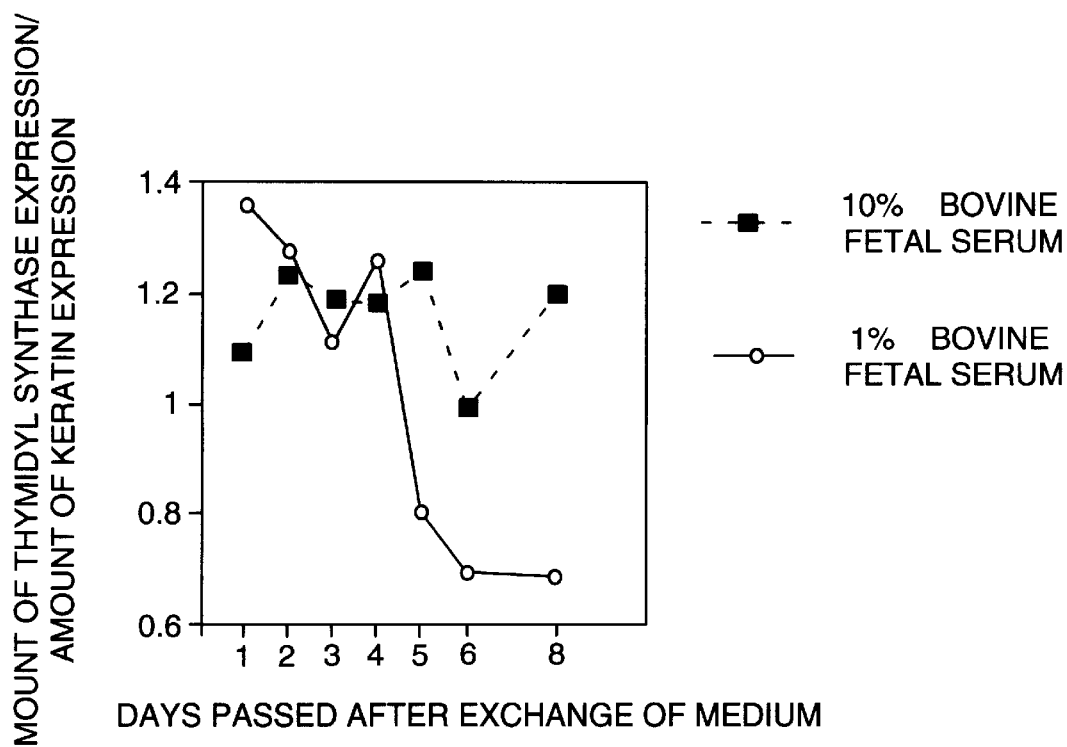
FIG. 1 shows the ratio of the band intensity of keratin band of each sample to that of thymidyl synthase changing days passed after exchange of medium in example 1.

Bovine mammary gland epithelial cells obtained by centrifugation of colostrum were cultured into a dense state in growth medium (DMEM medium (Gibco BRL) with 10% bovine fetal serum). After culturing into a dense state, the medium was abandoned and the cells were washed with PBS three times, followed by dividing them into a cultured group in growth medium and a cultured group with serum restricted medium and keeping them cultured. As a serum restricted medium, DEME medium with 1% bovine fetal serum was used. On day 1, 2, 3, 4, 5, 6, and 8 after the culture began, RNA was extracted from the cells of each group and was used for synthesis of cDNA with an antisense primer of bovine thymidyl synthase mRNA and PCR was carried out by using a primer of bovine thymidyl synthase. In the same way, cDNA was synthesized using an antisense primer of bovine basic (type 2) component type 3 keratin mRNA and PCR was carried out by using a primer of bovine basic (type 2) component 3 type keratin mRNA. PCR amplified products were separated by 2% agarose gel electrophoresis, visualized by ethidium bromide staining and the image was incorporated into a computer with a scanner. The stained intensity of the object band of thymidyl synthase in each sample and that of the object band of keratin was numeralized by image analysis software. Using these numerals, the ratio of band intensity of thymidyl synthase to that of keratin was calculated. The ratio of each sample was shown in FIG. 1.

From these results, in the cells cultured in a serum restricted medium, expression amount of thymidyl synthase after day 5 of the culture was largely lowered comparing with that of the cells cultured in growth medium. This made it clear that epithelial cells could be synchronized into $G_0$ phase by culturing epithelial cells in a serum restricted medium for 5 days or more.

Example 2
Method of Screening Using $G_0$ Phase Synchronized Cells

Figure 2:
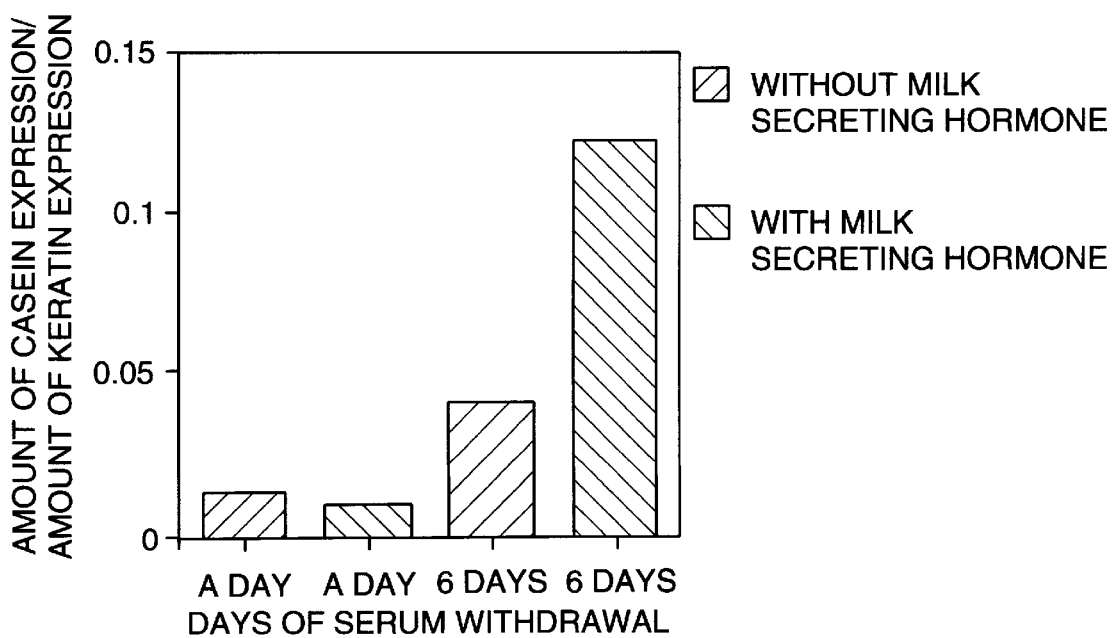
FIG. 2 shows the ratio of the amount of $\alpha_{s1}$-casein expression to that of keratin expression of each sample with or without milk secreting hormone, changing days of serum withdrawal in example 2.

Bovine mammary gland epithelial cells were cultured to confluence in a growth medium (DMEM medium (Gibco BRL) with 10% bovine fetal serum) and kept cultured for another 1 day after the medium was exchanged into bovine fetal serum free DMEM medium. These cells were divided into a cultured group in MCDB170 medium with insulin and hydrocortisone and a cultured group in MCDB medium with insulin, hydrocortisone, prolactin and growth hormone and kept cultured. One hour after the initiation of the culture, RNA was extracted and, according to the method described in example 1, RT-PCR of $\alpha_{s1}$-casein and keratin, so that the ratio of the amount of $\alpha_{s1}$-casein expression to the amount of keratin expression was determined. In the same way, bovine mammary gland epithelial cells were cultured to confluence in a growth medium and the medium was exchanged into DMEM medium with 1% bovine fetal serum and kept cultured for 6 days. Then, these were divided into a cultured group in MCDB medium with insulin and hydrocortisone and a cultured group in MCDB medium with insulin, hydrocortisone, prolactin and growth hormone and kept cultured. One hour after the initiation of the culture, RNA was extracted and the ratio of the amount of $\alpha_{s1}$-casein expression to the amount of keratin expression was determined. These results were shown in FIG. 2.

From the results, an effect of prolactin and growth hormone inducing differentiation was confirmed, because $\alpha_{s1}$-casein expression was observed in a group with the addition of prolactin and growth hormone when the cells were cultured in 1% bovine fetal serum for 6 days, though $\alpha_{s1}$-casein expression was not observed when the cells were once treated by serum withdrawal using a bovine fetal serum free medium for 1 day and cultured even in a medium with prolactin and growth hormone. From this result, it was found it possible to screen easily a factor inducing differentiation of mammary gland epithelial cell using synchronized cultured cells.

We claim:

1. A method of synchronizing epithelial cells in $G_0$ phase, comprising:

culturing said epithelial cells in a growth medium until they reach confluence;

removing said growth medium;

adding a serum-restricted medium, said serum-restricted medium having a concentration of serum of 5% or less; and growing said epithelial cells in said serum-restricted medium for five days without replacing the medium.

2. The method of claim 1, wherein said serum-restricted medium comprises less than 5% bovine fetal serum.

3. The method of claim 1, wherein said serum-restricted medium comprises less than 1% bovine fetal serum.

4. The method of any of claims 1–3, wherein said cells are bovine mammary epithelial cells.

5. The method of any of claims 1–3, wherein said medium is DMEM or MEM medium.

6. A method of culturing epithelial cells, comprising:

culturing said cells in a growth medium until they reach confluence;

removing said growth medium;

adding a serum restricted medium, said serum-restricted medium having a concentration of serum of 5% or less;

growing said epithelial cells in said serum-restricted medium for five days without replacing the medium, thereby producing $G_0$ phase synchronized cells; and culturing said $G_0$ phase synchronized cells.

7. A method of screening for a factor related to differentiation and/or maturation of cells, comprising:

culturing cells in a growth medium until they reach confluence;

removing said growth medium;

adding a serum-restricted medium, said serum-restricted medium having a concentration of serum of 5% or less;

growing said epithelial cells in said serum-restricted medium for five days without replacing the medium, thereby producing $G_0$ phase synchronized cells;

adding a candidate factor to said $G_0$ phase synchronized cells; and determining whether said cells differentiate and/or mature.

8. The method of claim 7, wherein said serum-restricted medium comprises less than 5% bovine fetal serum.

9. The method of claim 7, wherein said serum-restricted medium comprises less than 1% bovine fetal serum.

10. The method of 7, wherein said cells are bovine mammary epithelial cells.

* * * * *